United States Patent [19]

Yen-Maguire et al.

[11] Patent Number: 5,242,806
[45] Date of Patent: Sep. 7, 1993

[54] METHOD FOR CONDUCTING THE CYTOTOXICITY ASSAYS ON TUMOR CELLS

[75] Inventors: Yu P. Yen-Maguire, Bellevue; Tom Cox, Redmond; Fred Lewis, Bonney Lake, all of Wash.

[73] Assignee: Baxter Diagnostics Inc., Deerfield, Ill.

[21] Appl. No.: 884,604

[22] Filed: May 15, 1992

Related U.S. Application Data

[63] Continuation of Ser. No. 520,311, May 7, 1990, abandoned.

[51] Int. Cl.$^5$ .......................... C12Q 1/18; C12Q 1/20; C12M 1/34
[52] U.S. Cl. .......................... 435/32; 435/4; 435/29; 435/33; 435/291
[58] Field of Search .......................... 435/29, 34, 240.23, 435/240.24, 240.2, 287, 288, 291, 240.3, 240.31, 4, 32, 33

[56] References Cited

U.S. PATENT DOCUMENTS

| | | | |
|---|---|---|---|
| 3,992,265 | 11/1976 | Hangen | 435/33 |
| 4,153,512 | 5/1979 | Messner et al. | 435/33 |
| 4,357,422 | 11/1982 | Gard et al. | 435/70.5 |
| 4,411,990 | 10/1983 | Salmon et al. | 435/29 |
| 4,435,508 | 3/1984 | Gabridge | 435/284 |
| 4,496,657 | 1/1985 | Coppersmith et al. | 435/293 |
| 4,537,860 | 8/1985 | Tolbert | 435/240 |
| 4,559,299 | 12/1986 | Rotman | 435/3 |
| 4,599,314 | 7/1986 | Shami | 435/287 |
| 4,657,867 | 4/1987 | Guhl | 435/284 |
| 4,686,194 | 8/1987 | Bartos | 436/536 |
| 4,757,017 | 7/1988 | Cheung | 435/240.24 |
| 4,761,378 | 8/1988 | Godsey | 435/298 |
| 4,816,395 | 3/1989 | Hancock | 435/29 |
| 4,877,777 | 10/1989 | DiLuzio | 514/54 |
| 4,917,793 | 4/1990 | Pitt | 210/94 |
| 4,937,187 | 6/1990 | Rotman | 436/63 |
| 4,975,278 | 12/1990 | Senter et al. | 514/27 |
| 4,975,526 | 12/1990 | Kuberasampath et al. | 530/356 |
| 5,032,508 | 7/1991 | Naughton et al. | 435/32 |
| 5,036,008 | 3/1991 | Ohkuma et al. | 435/117 |

OTHER PUBLICATIONS

Alberts, D.S. et al., "Improved Survival for Relapsing Ovarian Cancer (OV CA) Patients (PTS) Using the Human Tumor Stem Cell Assay (HTSCA) to Select Chemotherapy (CRx)" ASCO Abstracts, 1981.

Alberts, David S. et al., "Pharmacologic Studies of Anticancer Drugs with the Human Tumor Stem Cell Assay", Cancer Chemother. Pharmacol. (1981) 6:253-264.

Alberts, David S. et al., "Tabular Summary of Pharmocokinetic Parameters Relevant to In Nitro Drug Assay", Cloning of Human Tumor Stem Cells, pp. 351-359.

Barnes, David et al., "Methods for Growth of Cultured Cells in Serum-Free Medium," Anal. Biochem, 102, 255-270 (1980).

Biotechnology Newswatch, Jun. 20, 1988, p. 7.

Crickard, Kent et al., "Human Ovarian Carcinoma Cells Maintained on Extracellular Matrix versus Plastic," Cancer Research 43, 2762-2767, Jun. 1983.

Daidone, Maria Grazia et al., "Reliability of an In Vitro Short-Term Assay to Predict the Drug Sensitivity of Human Breast Cancer," Cancer 56:450-456, 1985.

Earl-Clay Laboratories, Inc. "Ultraclone Oncoscreening System 6 Drug Assay".

Gospodarowicz, Denis et al., "Extracellular Matrix and Control of Proliferation of Fascular Endothelial Cells", J. Clin. Invest. vol. 65 Jun. 1980 1351-1364.

(List continued on next page.)

Primary Examiner—Jill A. Johnston
Attorney, Agent, or Firm—Kent Barta; Cynthia Tymeson; Paul C. Flattery

[57] ABSTRACT

A method and apparatus for assaying the sensitivity of biopsied tumor cells to chemotherapeutic agents using a predetermined amount of chemotherapeutic agent in an easily deliverable form is disclosed and claimed.

17 Claims, 5 Drawing Sheets

OTHER PUBLICATIONS

Hamburger, Anne W., "The Human Tumor Clonogenic Assay as a Model System in Cell Biology", Internatl. Journal of Cell Cloning 5:89–107 (1987).

Hamburger, Anne W., "Primary Bioassay of Human Tumor Stem Cells", Science vol. 197, Jul. 29, 1977, pp. 461–463.

Hanauske, Axel R. et al., "Clinical Correlations with the Human Tumor Cloning Assay", Cancer Investigation, 3(6), 541–551 (1985).

Kern, David H., et al., "Development of a Miniaturized, Improved Nucleic Acid Precursor Incorporation Assay for Chemisensitivity Testing of Human Solid Tumors", Cancer Research 45, 5436–5441, Nov. (1985).

Oncotech, "Put Our Research Team to Work for You".

Pavelic, L. et al., "Growth of Human Urological Tumors on Extracellular Matrix as a Model for the In Vitro Cultivation of Primary Human Tumor Explants," Cancer Research 46, 3653–3662, Jul. (1986).

Schelthauer, Werner et al., "Model for Estimation of Clinically Achievable Plasma Concentrations for Investigational Anticancer Drugs in Man," Cancer Treatment Reports vol. 70, No. 12, pp. 1379–1382.

Sevin, B.U. et al., "Application of an ATP-Bioluminescence Assay in Human Tumor Chemosensitivity Testing," Gynecologic Oncology 31, 191–204 (1988).

Shoemaker, R. H. et al., "Application of the Human Tumor Clonogenic Assay to Drug Screening".

Shoemaker, Robert H. et al., "Application of a Human Tumor Colony-forming Assay to New Drug Screening," Cancer Research 45, 2145–2153, May (1985).

Shoemaker, Robert H. et al., "Use of the Human Tumor Clonogenic Assay for New Drug Screening," AACR Abstracts, 1983.

Sirkin, Benita, "Earl-Clay Laboratories Begins Clinical Trials on Drug Sensitivity Test", Genetic Engineering News–Feb. 25, 1987.

Tanigawa, Nobuhiko et al., "Rapid Assay for Evaluating the Chemosensitivity of Human Tumors in Soft Agar Culture", Cancer Research 42, 2150–2164, Jun., 1982.

Volodavsky, I. et al., "Morphological Appearance, Growth Behavior and Migratory Activity of Human Tumor Cells maintained on Extracellular Matrix versus Plastic", Cell. vol. 19, 607–616, Mar. 1980.

Von Hoff, Daniel D., "In Vitro Methods to Predict for Patient Response to Chemotherapy" Adv. in Pharmacology and Chemotherapy, v. 17, pp. 133–157.

Von Hoff, Daniel D., "In Vitro Predictive Testing: the Sulfonamide Era," Int. J. of Cell Cloning 5:179–190 (1987).

Von Hoff, Daniel D. et al., "Association Between Human Tumor Colony-Forming Assay Results and Response of an Individual Patient's Tumor to Chemotherapy", The Amer. J. of Medicine, v. 70, pp. 1027–1032.

Von Hoff, Daniel D. et al., "Prospective Clinical Trial of a Human Tumor," Cancer Research 43, 1926–1931, Apr. 1983.

Wilson, A. P. et al. "A Comparison of Three Assays Used for the In Vitro Chemosensitivity Testing of Human Tumors," Br. J. Cancer 91984), 49, 57–61.

ADRIAMYCIN™

BLEOMYCIN™

METHOD FOR CONDUCTING THE CYTOTOXICITY ASSAYS ON TUMOR CELLS

"This is a continuation of application Ser. No. 7/520,311, filed on May 7, 1990 now abandoned."

BACKGROUND OF THE INVENTION

1. Field of the Invention this invention relates to a method and apparatus for conducting cytotoxicity assays on human biopsied tumor cells.

2. Description of the Prior Art

In 1955, Karnofsky presented to an audience of skeptics the ability of alkylating agents and antimetabolites to exhibit some chemotherapeutic activity in a limited number of human tumors. Tumor chemotherapy has greatly advanced since then and maintains an important role in the treatment of many tumors. Currently, chemotherapy can cure more than 16 tumor types, including hematological neoplasms; sarcomas; testicular, gestational, trophoblastic, and Wilm's tumors; and small cell lung and ovarian cancers. Other tumors curable in the adjuvant setting are breast and colon cancers. Advances in chemotherapeutics are ongoing: more effective drugs, drug analogs with less toxicity, and drugs modified for improved tissue uptake and longer plasma half life are being developed. DeVita, V.T. Jr, *Cancer Principles and Practice of Oncology*, Principles of Chemotherapy (V.T. DeVita, Jr., S. Hellman, S.A. Rosenberg eds.), J.B. Lippincott Co., Philadelphia, Pa., 1989.

Currently, tumor chemotherapeutic treatment is based upon standard practices resulting from empirical drug selection or established protocols. Von Hoff, D.D., L. Weisenthal, *In Vitro Methods to Predict for Patient Response to Chemotherapy*, Advances in Pharmacology and Chemotherapy, 17:133-156, 1980. Woltering, Eugene A., *Administration of Cytotoxic Chemotherapeutic Agents Without Predictive Information*, Laboratory of Medicine, 21:82, 1990. Variations in patient response to standard therapy are often the result of the highly heterogeneous nature of human tumors, both among different tumor types and within the same tumor type in an individual patient. This heterogeneity is reflected in the chemosensitivity of malignant cells. Variations in response can render unattainable the primary goals of chemotherapy—to maximize the effects of therapy on the tumor and to prevent side effects of therapy for the patient. Chemotherapy can offer the best chance of survival but it also has adverse effects that can be devastating, such as patient toxicity, immune system suppression, loss of time due to an ineffective treatment regimen, and the development of drug resistance.

A predictive assay is particularly important for cancer chemotherapy since is identifies ineffective drugs whose side effects are potentially life-threatening. The development of an in vitro assay which could predict the response of an individual's tumor cells to chemotherapeutics has been a longstanding objective in cancer research. The pioneers in this field include: Hamburger, Q.W., and S.E. Salmon, *Primary Bioassay of Human Tumor Stem Cells*, Science, 197:461-463, 1977, Hamburger, Anne W., *The Human Tumor Clonogenic Assay as a Model System in Cell Biology*, International Journal of Cell Cloning, 5:89-107, 1987, Scheithauer, W., G.M. Clark, S.E. Salmon, W. Dorda, R.HY. Shoemaker, D.D. Von Hoff, *Model for Estimation of Clinically Achievable Plasma Concentrations for Investigational Anticancer Drugs in man*, Cancer Treatment Reports, 70:1379, Shoemaker, R.H., M.K. Wolpert-DeFilippes, R.W. Makuch, *Application of the Human Tumor Clonogenic Assay for New Drug Screening*, Stem Cells, 1:308, 1981, Shoemaker, R.H., M.K. Wolpert-DeFilippes, R.W. Makuch, *Use of the Human Tumor Clonogenic Assay for New Drug Screening*, Proc. Amer. Assoc. Cancer Research, 24:1231, 1983, Shoemaker, R.H., M.K. Wolpert-DeFilippes, J.M. Venditti, IV., *Human Tumors in the Screening of Cytostatics*, Behring Inst. Mitt., 74:262, 1984, Alberts, D.S., H.S.G. Chen, *Cloning of Human Tumor Cells, (S.E. Salmon ed.)*, 351-359, Alan R. Liss, Inc., New York, N.Y., 1980, Alberts, D.S., H.S.G. Chen, L. Young, T.E. Moon, S.A. Loesch, E.A. Surwit, S.E. Salmon, *Improved Survival for Relapsing Ovarian Cancer (OVCA) Patients Using the Human Tumor Stem Cell Assay (HTSCA) to Select Chemotherapy*, Proc. Am. Assoc. Cancer Research, 22:461, 1981, Alberts, D.S., S.E. Salmon, E.A. Surwit, H.S.G. Chen, T.E. Moon, L. Young, *Combination Chemotherapy (CRx) In Vitro With the Human Tumor Stem Cell Assay (HTSCA)*, Cancer Chemother, Pharmcol., 6:253, 1981, Von Hoff, Daniel D., James Casper, Edward Bradley, John Sandbach, Donna Jones, Robert Makuch, *Association Between Human Tumor Colony-Forming Assay Results and Response of an Individual Patient's Tumor to Chemotherapy*, American Journal of Medicine, 70:1027-1032, 1981., Von Hoff, Daniel D., Gary M. Clark, Brian J. Stogdill, Michael F. Sarosdy, Michael T. O'Brien, James T. Casper, Douglas E. Mattox, Carey P. Page, Anatolio B. Cruz, and John F. Sandbach, *Prospective Clinical Trial of a Human Tumor Cloning System*, Cancer Research, 43:1926-1931, 1983, Hanauske, Axel-R., Daniel D. Von Hoff, *Clinical Correlations with the Human Tumor Cloning Assay*, Cancer Investigation, 3(6):541-551, 1985., Von Hoff, Daniel D., *In Vitro Predictive Testing: The Sulfonamide Era*, International Journal of Cell Cloning, 5:179-190, 1987, Von Hoff, Daniel D., *Commentary, He's Not Going to Talk About In Vitro Predictive Assays Again, Is He?*, Journal of the National Cancer Institute, 82:96-101, 1990.

Current in vitro chemosensitivity methods include: clonging of human tumors on double layer soft agar, i.e. human tumor cloning assay (HTCA); subrenal capsule assay method, fluorescent cytoprint assay (Rotman RIVCA) and tritiated thymidine uptake assay.

The traditional in vitro method of growing human tumor cells in semi-solid agar developed by Salmon and Hamburger is referred to as the human tumor clonging assay (HTCA). In this method, solid tumors or malignant fluid from cancer patients may be used as the tumor cell source. The tumor specimens are mechanically and enzymatically dissociated to fulfill the requirement of a single-cell suspension. When short-term drug treatment is being evaluated, the single-cell suspension is incubated in media with or without the therapeutic drug. After the cells are exposed to the drug for one hour, control and treated cells are plated on agar. For continuous drug treatment, the drug is added directly to the top agar layer containing cells in a 2-layer system. In both cases, the cells are incubated for 14-21 days and observed for colony formation. The difference in the number of colonies counted in plates containing drug treated cells and in control plates is used to determine drug responsiveness, Shoemaker, Robert H., Mary K. Wolpert-DeFilippes, David H. Kern, Michael M. Lieber, Robert W. Makuch, Jeannete R. Melnick, William T. Miller, Sydney E. Salmon, Richard M. Simon, John M. Venditti and Daniel D. Von Hoff, *Application of a Human Tumor Colony Forming Assay to a New Drug Sensitivity*, Cancer Research, 45:2145-2153, 1985, Woltering, Eugene A., *Tumor Chemosensitivity Testing: An Evolving Technique*, Laboratory Medicine, 2:82-84, 1990.

The subrenal capsule assay method differs from the traditional HTCA by utilizing tumor fragments, measuring the responsiveness of multiple cell populations rather than single-cell suspensions. Subrenal capsule is an in vivo assay utilizing human tumor specimens as first-generation transplant xenografts in athymic mice. The predictability of drug resistance with the subrenal capsule assay has not been found to be superior to the HTCA. The greatest advantage is that more tumor specimens can be successfully grown using subrenal capsule than HTCA, Woltering, Eugene A., *Tumor Chemosensitivity Testing: An Evolving Technique*, Laboratory Medicine, 2:82-84, 1990. However, due to the expense involved in maintaining mouse colonies and the technical expertise required, the subrenal capsule assay has not become a routine test.

Rotman and coworkers have developed an in vitro chemosensitivity method (RIVCA) also referred to as the fluorescent cytoprint assay (FCA). In this assay, tumor fragments are exposed to the drug and cultured. The viability of the tumor cells is measured by their ability to hydrolyze fluoresce in diacetate and retain the fluorescein. The difference in the number of fluorescent fragments before and after drug treatment is used as a measure of drug response. RIVCA is not amenable to fluid specimens or to solid specimens yielding small cell aggregates, since only aggregates larger than 50-100 cells can be photographically recorded. The predictability of drug resistance with RIVCA is similar to that of HTCA, but a greater number of tumors can be grown in vitro and evaluated using RIVCA, Woltering, Eugene A., *Tumor Chemosensitivity Testing: An Evolving Technique*, Laboratory Medicine, 2:82-84, 1990.

Due to difficulties in obtaining single-cell suspensions from solid tumors, long incubation times, and poor tumor growth in the HTCA, alternative methods have been evaluated. One of these methods uses the incorporation of a radionucleotide, such as tritiated thymidine, during DNA synthesis as an indication of cell viability and proliferation. Tumor preparations are exposed to drugs, either short-term or continuously, and cultured in liquid medium. Tritiated thymidine is added and the culture incubated for 16-24 hours. Incorporated radionucleotides are harvested and counted with a scintillation counter. A decrease in the uptake of tritiated thymidine by tumor cells exposed to cancer chemotherapeutics indicates sensitivity of the tumor to the drug. This assay has several advantages over HCTA, SRA, and RIVCA: a shorter culture period (4-6 days) is required, a smaller sample size can be assayed, and the strict requirement for single-cell suspensions—a goal often unachievable for solid tumors—is eliminated. Another benefit of this assay is that the determination of tumor growth is quantitative and automated, in contrast to the subjective counting of colonies by a tissue culture technician. The clinical relevance of a radionucleotide detection system in an in vitro chemosensitivity assay has been documented: Kern, David H., Carol R. Drogemuller, Michale C. Kennedy, Susanne U. Hioldebrand-Zanki, Nobuhiko Tanigawa, and Vernon K. Sondak, *Development of a Miniaturized, Improved Nucleic Acid Precursor Incorporation Assay for Chemosensitivity Testing of Human Solid Tumors*, Cancer Research, 45;5435-5441, 1985; Daidone, Maria Grazia, Rosella Silvestrini, Ornella Sanfilippo, Nadia Zaffaroni, Marco Varini, Mario Delena, *Reliability of an In Vitro Short-Term Assay to Predict the Drug Sensitivity of Human Breast Cancer*, Cancer, 56:450-14 456, 1985, Tanigawa, Nobuhiko, David H. Kern, Yorinori Hikasa, and Donald L. Morton, *Rapid Assay for Evaluating the Chemosensitivity of human Tumors in Soft Agar Culture*, Cancer Research, 42:2159-2164, 1982, Wilson, A.P., C.H.J. Ford, C.E. Newman, A. Howell, A Comparison of Three Assays Used for the In Vitro Chemosensitivity Testing of Human Tumours, British Journal of Cancer, 49:57-63, 1984. One group of investigators assaying cells from a variety of solid tumor types (breast, lung, and ovarian cancers, melanomas and sarcomas) found that 80% of the specimens were evaluable (280/351) with 100% accuracy in predicting resistance and 50% accuracy in predicting sensitivity. Kern, David H., Carol R. Drogemuller, Michael C. Kennedy, Susanne U. Hildebrand-Zanki, Nobuhiko Tanigawa, and Vernon K. Sondak, *Development of a Miniaturized, Improved Nucleic Acid Precursor Incorporation Assay for Chemosensitivity Testing of Human Solid Tumors*, Cancer Research, 45:4335-5441, 1985. In another report, assaying only cells derived from breast cancers, the prediction of tumor sensitivity and resistance was 75% and 81% accurate, respectively. Daidone, Maria Grazia, Rosella Silvestrini, Ornella Sanfilippo, Nadia Zaffaroni, Marco Varini, Mario DeLena, *Reliability of an In Vitro Short-Term Assay to Predict the Drug Sensitivity of Human Breast Cancer*, Cancer, 56:450-456.

In order to conduct tumor sensitivity assays the tumor must be maintained in culture. Epithelial cells are the select culture medium in this field. In a recently published report, Von Hoff, Daniel D., *Commentary, He's Not Going to Talk About In Vitro Predictive Assays Again, Is He?*, Journal of the National Cancer Institute, 82:96-101, 1990, based on nearly 14,000 tumor samples, only 3,886 or 27.9% had sufficient in vitro growth for evaluation of drug sensitivity. Recent modifications of culture conditions and the development of sensitive detection methods have increased the capacity to obtain evaluable specimens. Hanauske, Axel-R., Daniel D. Von Hoff, *Clinical Correlations with the Human Tumor Cloning Assay*, Cancer Investigation, 3(6):541-551, 1985, Shoemaker, Robert H., Mary K. Wolpert-DeFilippes, David H. Kern, Michael M. Lieber, Robert W. Makuch, Jeannete R. Melnick, William T. Miller, Sydney E. Salmon, Richard M. Simon, John M. Venditti, and Daniel D. Von Hoff, *Application of a Human Tumor Colony Forming Assay to New Drug Sensitivity*, Cancer Research, 45:2145-2153, 1985. The specific problem of inadequate in vitro tumor growth has been explored extensively. To achieve adequate tumor growth, a defined, selective medium is required that allows tumor cells, most commonly of epithelial origin, to actively proliferate while inhibiting the proliferation of normal cells, such as fibroblasts. It has become apparent, however, that "traditional" growth media and high serum concentrations are not optimal for epithelial tumor cell growth. Reid, Lola M., *Generic Methods for Defined Hormonal and Matrix Conditions for Studies of Growth or Gene Expression in Differentiated Epithelia*, Methods in Molecular Biology, (J.W. Pollard, J.M. Walker, eds.), Volume 5: Tissue Culture. Growth medium containing a high calcium (greater than 1 mM) and high serum (10-25%) concentration enhances the proliferation of fibroblasts. In contrast, epithelial cells exhibit the best growth in a low calcium (approximately 0.4 mM) and a low serum (1% and below) environment. Additionally, serum in the medium contributes to inconsistent results between assays due to lot-to-lot variations in the concentrations of several critical components in the serum. A low serum concentration in the medium reduces the impact of this variability. However, since epithelial tumor cells require specific growth factors and hormones which are present in the serum, reduction of the serum concentration necessitates the supplementation of those growth factors and hormones. Barnes, David and Gordon Satro, *Methods for Growth of Cultured Cells in Serum-Free Medium*, Analytical Biochemistry, 102:255-270, 1980. Therefore, a growth medium containing low calcium and serum concentrations supplemented with defined growth factors and hormones allows preferential growth of epithelial tumor cells, resulting in an increase in the number of evaluable specimens. Reid, Lola M., *Generic Methods for Defined Hormonal and Matrix Conditions for Studies of Growth or Gene Expression in Differentiated Epithelia*, Methods in Molecular Biology, (J.W. Pollard, J.M. Walker, eds.), Volume 5: Tissue Culture, Crickard, Kent, Ulla Crickard, Mahmood Yoonessi, *Human Ovarian Carcinoma Cells Maintained on Extracellular Matrix Versis Plastic*, Cancer Research, 43:2762-2767, 1983.

Roswell Park Memorial Institute 1640 (RPMI) (Life Technologies, Grand Island, N.Y.) is a basal medium containing inorganic elements, energy sources, vitamins, amino acids, and a low concentration of calcium (0.67 mM). RPMI, however, lacks the hormones and growth factors often necessary for proliferation of epithelial tumor cells. Various hormones and growth factors are typically added individually to the growth medium according to the requirements of the cell type being grown. Barnes, David and Gordon Sato, *Methods for Growth of Cultured Cells in Serum-Free Medium*, Analytical Biochemistry, 102:255-270, 1980, Ham, R.G., *Importance of the Basal Nutrient Medium in the Design of Hormonally Defined Media*, Cold Spring Harbor Laboratory, 9:39-60, 1982.

In a review of 2300 patients, the correlation between an in vitro chemosensitivity assay and actual patient response indicated that the predictability of true sensitivity is 69% and true negative predictability 91%. Scheithauer, W., G.M. Clark, S.E. Salmon, W. Dorda, R.H. Shoemaker, D.D. Von Hoff, *Model for Estimation of Clinically Achievable Plasma Concentrations for Investigational Anticancer Drugs in Man*, Cancer Treatment Reports, 70:1379, Von Hoff, Daniel D., James Casper, Edward Bradley, John Sandbach, Donna Jones, Robert Makuch, *Association Between Human Tumor Colony-Forming Assay Results and Response of an Individual Patient's Tumor to Chemotherapy*, American Journal of Medicine, 70:1027-1032, 1981, Von Hoff, Daniel D., Gary M. Clark, Brian J. Stogdill, Michael P. Sarosdy, Michael T. O'Brien, James T. Casper, Douglas E. Mattox, Carey P. Page, Anatolio B. Cruz, and John F. Sandbach, *Prospective Clinical Trial of a Human Tumor Cloning System*, Cancer Research, 43:1926-1931, 1983, Hanuske, Axel-R., Daniel D. Von Hoff, *Clinical Correlations With the Human Tumor Cloning Assay*, Cancer Investigation, 3(6):541-551, 1985. These correlations have been the result of either retrospective or prospective single-arm studies. Only two prospective randomized trials have been performed. One prospective study was conducted with ovarian cancer patients in which the response rates, though not statistically significant, were 65% for the standard chemotherapy arm and 85% for treatment based on in vitro assay results. Welander, C.E., T.M. Morgan, H.D. Homesley, *Multiple Factors Predicting Responders to Combination Chemotherapy in Patients With Ovarian Cancer*, In Human Tumor Cloning (S.E. Salmon, J.M. Trent eds.) Orland: Grune and Stratton, 521-534, 1984. A larger scale prospective randomized trial was conducted on 133 advanced metastatic cancer patients. Patient response rates were 21% for those who received single-agent chemotherapy based on in vitro assay results and only 3% in patients who received a clinician's choice of a single agent. Von Hoff, Daniel D., *Commentary, He's Not Going to Talk About In Vitro Predictive Assays Again, Is He?*, Journal of the National Cancer Institute, 82:96-101, 1990. These studies begin to supply reliable data supporting the general use of an assay to predict patient response to chemotherapeutics.

An in vitro chemoresponse assay is not in general use because of a number of obstacles which have contributed to the lack of clinical feasibility of the assay. Currently, in vitro drug response assays are performed in university hospitals and a few specialized service centers. These institutions generally require the transportation of the specimen, resulting in a loss of often more than 24 hours before specimen processing can begin. Within this 24 hour period, specimen viability declines significantly. Additionally, an in vitro assay is not in general use because of the lack of truly effective cancer drugs and difficulties in trying to model in vivo pharmacokinetics. Other reasons why in vitro chemoresponse tests are not in general use include: technical complexity of the assays; the inability to grow tumor cells in vitro; long turn-around time; large number of tumor cells required to conduct an assay; low percentage of specimens suitable for the assay; and the lack of quality control for drugs and medium.

SUMMARY OF THE INVENTION

The present invention relates to a method for assaying the sensitivity of biopsied tumor cells to chemotherapeutic agents, the method comprising incubating tumor cells with a sufficient amount of growth medium to form a cellular suspension, adding said cellular suspension to a first multi-compartment vessel; adding a predetermined amount of at least one chemotherapeutic agent in the dry form to a second multi-compartment vessel; adding a sufficient amount of said medium to reconstitute said dry chemotherapeutic agent to within physiologically reachable dosage ranges; adding reconstituted chemotherapeutic agent to certain compartments of said first vessel containing tumor cells; incubating said vessel for a sufficient period of time for said chemotherapeutic agent to affect said tumor cells; adding an indicator of tumor cell viability or growth to said first vessel; measuring the amount of said indicator, and comparing the amount of said indicator in said compartment to which said chemotherapeutic agent was added with the amount of said indicator in the compartment that did not receive said chemotherapeutic agents, to determine the sensitivity of said tumor cells for said chemotherapeutic agent. The first vessels may be coated with a growth matrix to increase specimen evaluability.

The present invention also relates to a kit to assay biopsied tumor cells for sensitivity to chemotherapeutic agents comprising: a) a first multi-compartment vessel for receiving said biopsied tumor cells; b) a second multi-compartment vessel for receiving predetermined amounts of at least one chemotherapeutic agent in the dry form; c) a sufficient amount of medium to support the growth of said tumor cells in said first multi-compartment vessel; d) a sufficient amount of medium to reconstitute said dry chemotherapeutic agent to within physiologically reachable dosage ranges; e) an indicator of cell proliferation or cell viability; and f) means for determining the percent of inhibition of cell growth or proliferation as a measure of said biopsied tumor cell sensitivity to said chemotherapeutic agents. In this case the first vessel may also be coated with a growth matrix to increase specimen evaluability.

It is an object of this invention to provide a method for assaying the sensitivity of biopsied cells to therapeutic agents using a small number of tumor cells.

It is an object of this invention to provide a 96-microwell coated with extracellular matrix to increase specimen evaluability and to permit assay automation. An extra cellular matrix is used to provide a natural stratum enhancing in vivo growth properties and biological responsiveness.

It is another object of this invention to provide a defined growth medium with minimal serum and calcium content to selectively enhance the growth and proliferation of epithelial tumor cells. It is still another object of this invention to enhance the proliferation of epithelial tumor cells with supplemental hormones and growth factors.

It is still another object of this invention to provide chemotherapeutic agents in a microwell drug strip, to facilitate selection of desired chemotherapeutics.

It is still another object of this invention to use tritiated thymidine uptake as an indicator of tumor cell viability to reduce the subjectivity of cell viability measurements. Tritiated thymidine uptake assay reduces specimen testing time from approximately 3 weeks to 5 days.

It is still another object of the invention to reduce technical complexity through the use of prepared drug strips and radionucleotide detection which can be automated and which does not require specialized training. This reduced technical complexity permits the use of an in vitro predictive assay in a clinical laboratory allowing the usage of fresh specimens. It is important to note that use of fresh specimens maximizes cellular viability.

DETAILED DESCRIPTION OF THE INVENTION

This kit is used to test the response of individual cancer patient's sensitivity and resistance to standard panel of anti-cancer drugs. Tumor specimens including those obtained from surgical specimens, malignant fluids, bone marrow or blood, are cultured either directly on tissue culture plastics, or tissue culture plastics with modified surface (coated with one or more extracellular matrices, fibronectin, collagens, or others; or surface charge modified by a variety of methods) for recovery. The dried drugs are reconstituted with growth medium and transferred to the wells containing the cells. The plates are incubated further for drugs to express their effect on cells. The growth of cells in drug containing wells or control wells (no drugs) is compared. A variety of methods used to assess proliferation including radionucleotide incorporation, dye reduction, or protein and nuclear stain can be employed. Inhibition of growth due to drugs as compared to the 100% controls is used to predict the probability of patient's response to drugs.

This kit is composed of a multi-compartment vessel, coated or not coated with a layer of growth matrix. The growth matrix can be either secreted by bovine cornea endothelium cells, or reconstituted basement membrane proteins or other proteins, matrices which facilitate cell attachment. The compartment can also be modified by adding electric charges to facilitate cell attachment.

The usage of the microtiter well, however, facilitates automation. Assay technology using chromogenic dyes, fluorogenic dyes can be read with ELISA plate reader or fluorogenic reader. In addition, the technique employing incorporation of radioactive labelled nucleotide or proteins as an indication of cell growth can be simplified by using the microtiter well. Incorporated radioactive compound can be harvested with a cell harvester.

Figure 2:
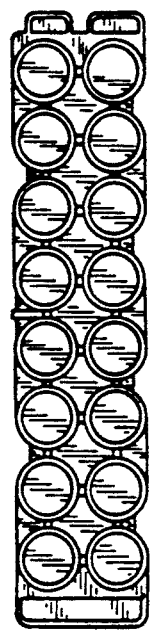
FIG. 2 shows a microwell drug strip.
Figure 3:
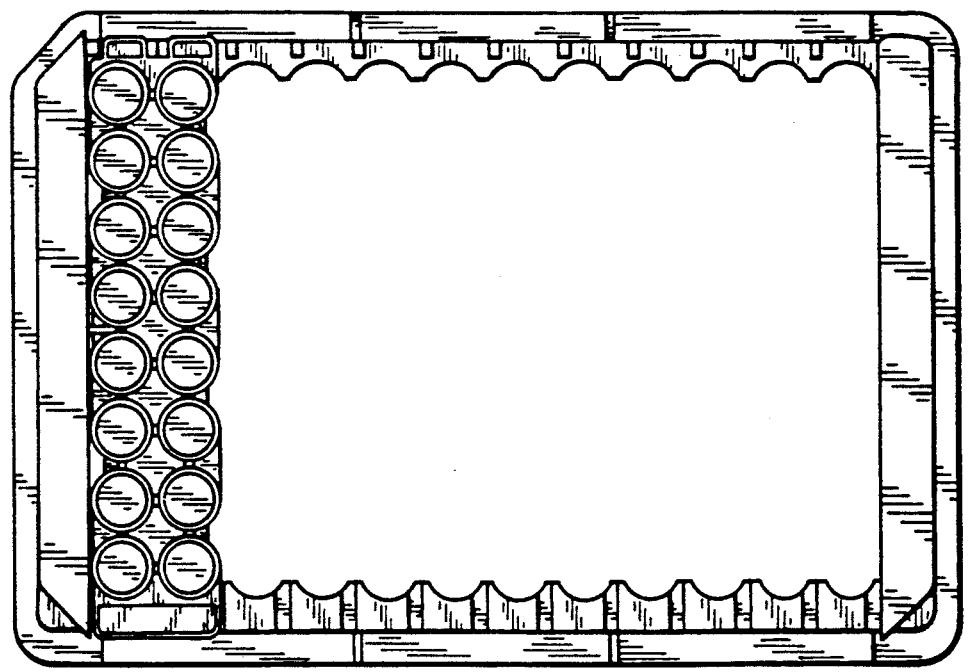
FIG. 3 shows a plate frame with a microwell drug strip.
Figure 4:
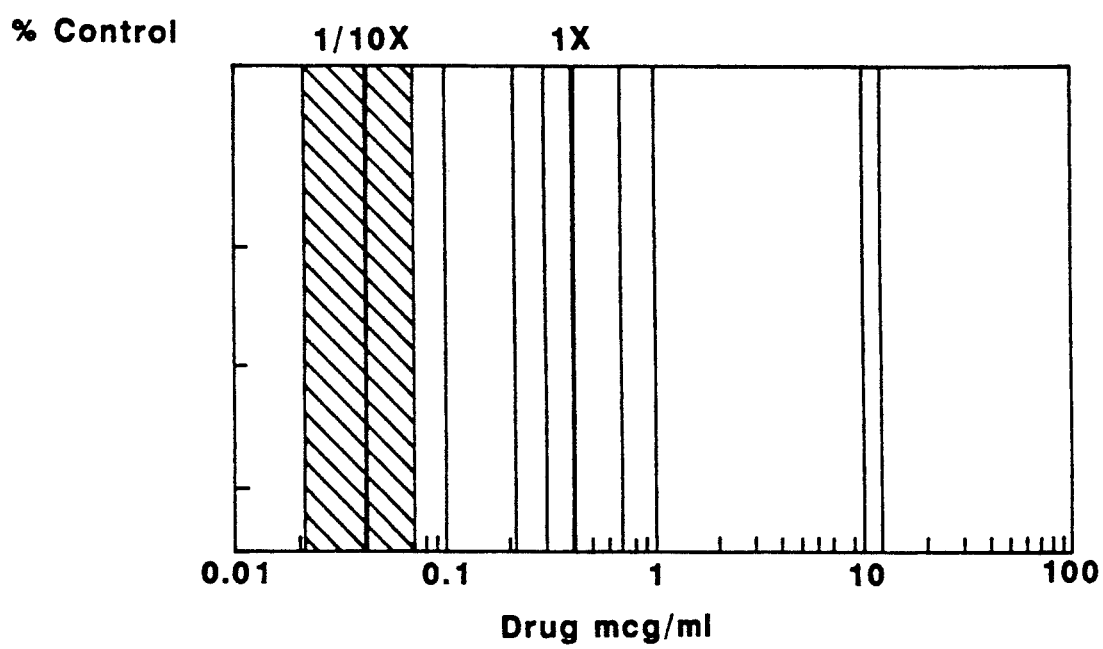
FIG. 4 shows assay results for sensitivity to Adriamycin TM.
Figure 5:
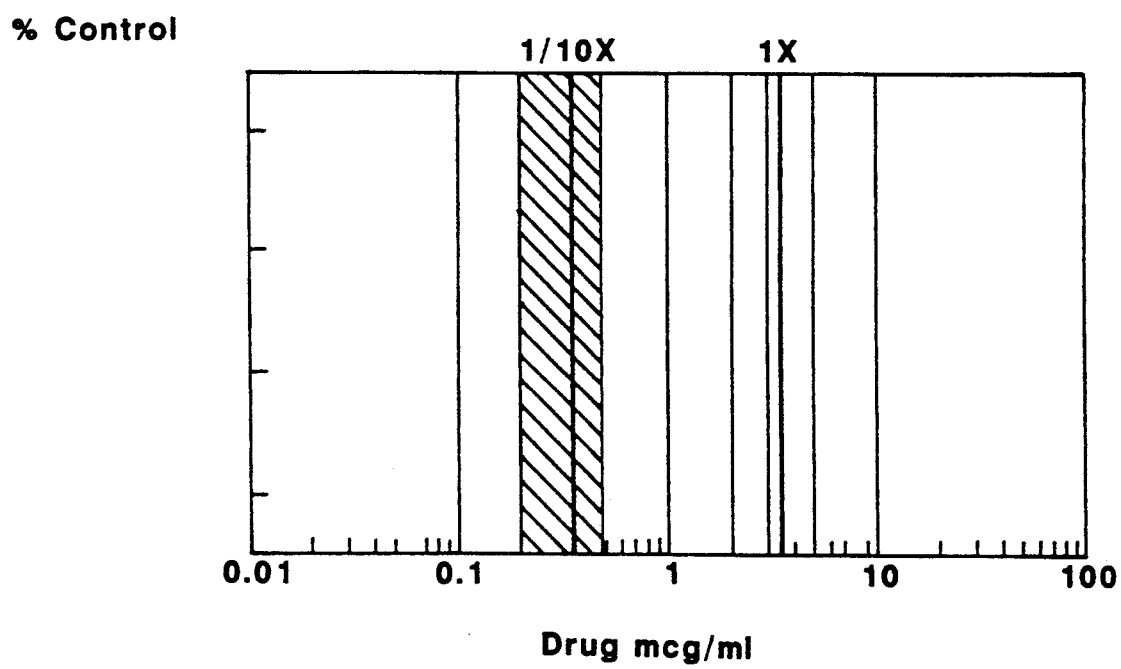
FIG. 5 shows assay results for sensitivity to Bleomycin TM.
Figure 6:
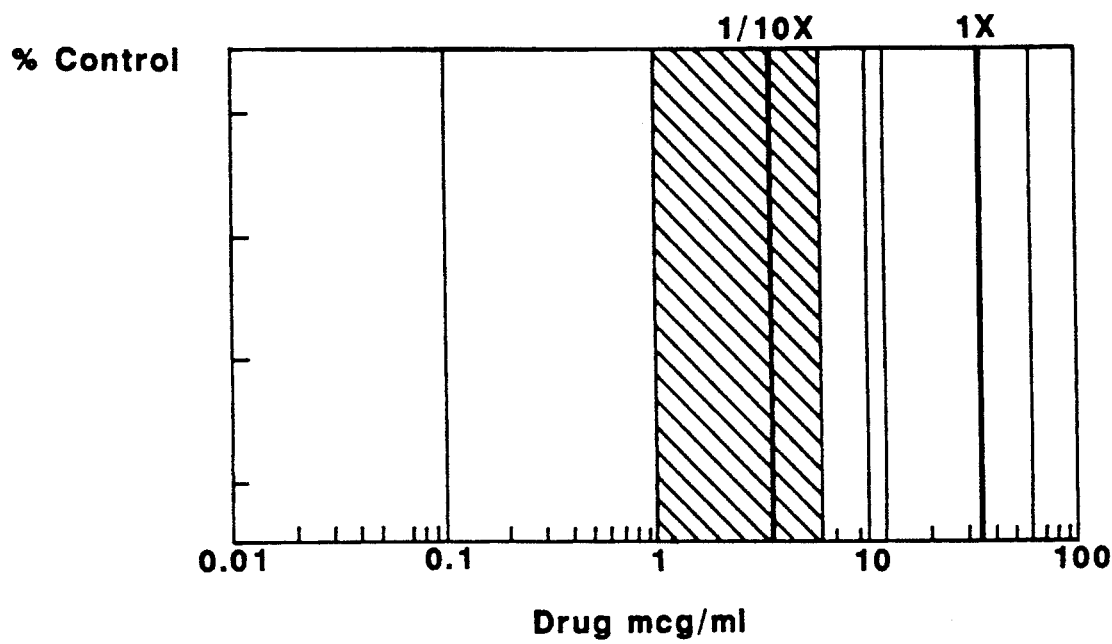
FIG. 6 shows assay results for sensitivity to 5-Fluorouracil TM.

The chemotherapeutic agents can be dried in strips. See FIG. 2. The strips fit into a housing with similar configuration as the microtiter well. FIG. 3. This configuration facilitates drug transfer with multiple channel pipettor. Chemotherapeutic agents at different predetermined concentrations are dispensed, quickly frozen and lyophilized. Dried drug strips are packaged in aluminum foil pouch or other air-and light-tight packaging material with desiccant, and sealed. The strip format allows the user to select desirable drugs.

Another feature of the kit is a medium and supplement which support the growth of human tumors. Conventionally, drug response assay is done at service labs because of the laborious process of drug dilutions, medium and matrix preparations and labor intensive method used to obtain results. In addition, there is no quality control for the reagents used for the test, ie, drugs, medium and medium supplement. This kit simplifies the technical complexity and problems and makes it possible to conduct the test at most hospital clinical laboratories.

Strips of microtiter wells are fit into a first multi-compartment vessel such as a 96 well microtiter plate. Plates other than 96-well plates may be used, ie, 6, 24, or 48 cluster plates or any other formats of multiple cluster plates. These plates come in the form of strip plates or the conventional culture plates.

Wells may or may not be coated with a layer of growth matrix.

Variations in the growth matrix, or tissue culture surface modifications include: extracted basement membrane proteins from various sources (ie, rat tail collagens, fibronectin, EHS transplantable tumors maintained in euthymic nude mice, matrix deposited by normal or tumor cell lines, etc). Tissue culture surface may be modified by treating the surface with electric corona discharge to facilitate cell attachment. Alternatively, matrix may not be used and drugs can be directly deposited on the tissue culture plastic surface.

Anti-cancer drugs are dispensed in replicates, at various predetermined concentrations, into the vessels and dried. Drugs may also be dried in vessels coated with any variety of matrices. The term "dried" means lyophilized or dried at low temperatures. Drugs may be dispensed into strips, ELISA plates, or vessels with a variety of configurations or tissue culture plastics. The strip format is used for two purposes: 1) to offer the user a choice of drugs to be tested; 2) to allow the cells to recover after initial processing before challenging cells with drugs. If cells do not need to recover, then tissue culture plates with dry drugs can be used to save the drug reconstitution and transfer step. In this case, cells can be directly plated in tissue culture plates containing the dry drugs. If drugs are dried on vessels other than where the cells are cultured, then drugs need to be reconstituted and transferred to the plate where the cells are cultured. Dried drug strips are packaged in air and light tight materials such as aluminum foil pouch with desiccant and sealed.

Specialized medium (RPMI medium with 1% fetal bovine serum), growth factor- and hormone-containing supplement (Cyto-Gro TM 289 supplement) and growth matrix capable of supporting the growth of tumor cells are included with the kit. Variations in the growth medium, and supplement growth medium may be any enriched buffer medium such as DMEM, F12, McCoy's, CMRL, etc, that is suitable for the growth of cells. Growth supplement may be any combination of growth factors and hormones included or not included in Cyto-Gro TM 289 supplement which promote the growth of cells being tested.

Fresh tumor specimens are collected and transported according to standard practices. The specimen is processed to obtain a cell suspension using mechanical and enzymatic digestion procedures and a differential count using trypan blue to assess viability. It should be noted that in the presently described procedure there must be at least $3 \times 10^5$ tumor cells to conduct the assay. If necessary, tumor cells are enriched with the use of Ficoll TM and Percoll TM density gradient separation methods.

The processed cells are suspended in defined growth medium consisting of Roswell Park Memorial Institute (RPMI) 1640 medium, 1% fetal bovine serum (FBS), and Cyto-Gro TM 289 supplement and aliquoted into an extra-cellular matrix coated 96-microwell tissue culture plate. Cyto-Gro TM 289 supplement was developed by Bartels Diagnostics with the goal of providing hormone and growth factor supplements for low serum growth medium to optimize epithelial tumor cell growth, thereby eliminating the need to inventory each additive separately. Cyto-Gro TM 289 supplement contains insulin, transferring, selenium, B-estradiol, hydrocortisone, prostaglandin F2a, and epidermal growth factor. RPMI, Cyto-Gro TM 289 supplement and a low concentration of serum (1%), combine to provide a growth medium with selective advantages for the growth of human epithelial tumor cells.

Maximum proliferation of epithelial cells is also dependent upon the presence of a substratum of extracellular matrix. Extracellular matrix is composed of different types of collagens, glycosaminoglycans, proteoglycan and glycoproteins. The use of extracellular matrix maximizes cell attachment and survival and has also been found to optimize the effect of hormones and growth factors in defined media. A number of adhesive cell matrices have been investigated, both natural and reconstituted. The use of naturally produced strata provides a more biologically similar growth matrix, assuring that the components are in a native configuration. Reconstituted extracellular matrices that have been explored include Matrigel TM, a urea extract from Engelbreth-Holm-Swarm mouse embryonal carcinoma, and biomatrix, placental tissue extracted by salt solutions, nucleases and detergents. Bovine cornea endothelium cells produce an extracellular matrix beneath the cell layer, which is the most commonly used extracellular matrix. Research has shown that when cells are grown on bovine cornea endothelium cells extracellular matrix monolayers are formed, with no aggregates or clumping. Even if cells are seeded as aggregates, the cells will spread out, Vladavsky, I., G.M. Lui and D. Gospodarowicz, *Morphological Appearance, Growth Behavior and Migratory Activity of Human Tumor Cell Maintained on Extracellular Matrix Versus Plastic*, Cell 607–616, March 1980. The formation of cell monolayers, promoted by extracellular matrix, aids in the optimization of the tritiated thymidine incorporation assay. The use of extracellular matrix has been shown to increase the number of specimens successfully cultured in vitro, 85–89% versus 59–60%, respectively. With prostate carcinoma, 89% of the specimens were evaluable when grown on extracellular matrix, but 0% were evaluable when grown on plastic. Renal tumors had an evaluability rate of 95% with extracellular matrix and 11% with plastic, Pavelic, K., M.A. Bulbul, H.K. Slocum, Z.P. Pavelic, Y.M. Rustum, M.J. Niedbala, and R.J. Bernacki, *Growth of Human Urological Tumors on Extracellular Matrix as a Model for the In Vitro Cultivation of Primary Human Tumor Explants*, Cancer Research, 46:3653–3662, 1986. Endometrial and ovarian carinoma which had not previously been maintained successfully in cell culture were 100% culturable with extracellular matrix. The increased success rate of tumor cell grown on extracellular matrix compared to plastic is a manifestation of cells being able to adopt in vivo growth properties by becoming physiologically responsive to hormones and growth factors, Crickard, Kent, Ulla Crickard, Mahmood Yoonessi, *Human Ovarian Carcinoma Cells Maintained on Extracellular Matrix Versus Plastic*, Cancer Research, 43:2762–2767, 1983, Pavelic, K., M.A. Bulbul, H.K. Slocum, Z.P. Pavelic, Y.M. Rustum, M.J. Niedbala, and R.J. Bernacki, *Growth of Human Urological Tumors on Extracellular Matrix as a Model for the In Vitro Cultivation of Primary Human Tumor Explants*, Cancer Research, 46:3653–3662, 1986, Vladavsky, I., G.M. Lui and D. Gospodarowicz, *Morphological Appearance, Growth Behavior and Migratory Activity of Human Tumor Cells Maintained on Extracellular Matrix Versus Plastic*, Cell 607–616, March 1980, Gospodarowicz, Denis, Charles III, *Extracellular Matrix and Control of Proliferation of Vascular Endothelial Cells*, Journal of Clinical Investigation, 65:1351–1364, 1980. These characteristics, increased evaluability, improved tritiated thymidine uptake due to cell monolayer formation, and responsiveness to growth medium components, make extracellular matrix especially valuable in a chemosensitivity assay, where an in vitro cell response is used as an indication of an in vivo tumor response.

The cells are allowed to recover for 24 hours in 37° C., 5% $CO_2$, humidified incubator before they are treated with the drug. Cancer chemotherapeutics lyophilized in a strip of 16 wells in a 2×8 format containing four different amounts of the drug are reconstituted with growth medium and added to cells. The four different concentrations are based on the plasma achievable level of the drug, along with a higher drug concentration to detect extremely resistant cells and two lower concentrations to quantity sensitive cells. The drugs that are currently available represent commonly prescribed cancer chemotherapeutics: Adriamycin TM, Bleomycin TM, Cisplatinol TM (cis-platin diamine dichloride), Etoposide TM, 5-Fluorouracil TM, Melphalan TM, Methotrexate TM, Mitomycin C TM, and Vinblastine sulfate.

The cells are incubated with the selected drugs for 3 days allowing the drug to express its effect. On the fifth day of post-specimen processing, tritiated thymidine at 1 microCurie per well is added. Incorporation of tritiated thymidine into nucleotides during DNA synthesis is used as an indication of cell growth. After the tumor cells have been exposed to the radionucleotide, the cells are harvested and the radionucleotide measured with a scintillation counter. The amount of radionucleotide incorporated into nucleic acid by the positive control which has not been exposed to a drug, is compared to that incorporated by drug treated cells and represented as counts per minute (CPM). The growth of resistant tumor cells, those not affected by the drug, will be comparable to those in the positive control wells and have similar radioactivity. Tumor cells sensitive to a drug will have a reduction in growth characterized by a reduction in DNA synthesis and demonstrated by a reduction in the uptake of tritiated thymidine, represented as CPM, when compared to the positive control. See FIG. 1.

Reagents and Materials 1. 96-microwell tissue culture plate with extracellular matrix derived from bovine cornea endothelium cells packaged in a foil pouch with a molecular sieve desiccant
2. Percoll TM isotonic 90% stock solution for gradient cell separation in specimen processing in a polyvinylpyrrolidone coated colloidal silica suspension, 15 ml (Parmacia Chemicals, Piscataway, N.J.)
3. Growth media: lyophilized Cyto-Gro TM 289 hormone and growth factor supplement to be reconstituted with basal media consisting of Roswell Park Memorial Institute medium (RPMI), (Life Technologies, Grand Island, N.Y.)+1% fetal bovine serum (HyClone Laboratories, Logan, Utah) reconstitute to 1 L
4. L-glutamine (Sigma, St. Louis, Mo.) 2 mM, 5 ml Asparagine (Sigma, St. Louis, Mo.) 0.5 mM, 5 ml
5. Microwell drug strips packaged in a foil pouch with a molecular sieve desiccant. See FIG. 2. Each drug strip contains 16 wells in a 2×8 format. The concentrations after reconstitution (μg/ml) are listed below and stated on the label of each strip. Available drugs to be tested include:

| Drug Name | Vendor | Supplied Concentrations (μg/ml) |
|---|---|---|
| Adriamycin TM | Adria Laboratories | 0.01, 0.1, 1.0, 10.0 |
| Bleomycin TM | Bristol-Myers | 0.01, 0.1, 1.0, 10.0 |
| Cisplatinol TM | Bristol-Myers | 0.01, 0.1, 1.0, 10.0 |
| Etoposide TM | Bristol-Myers | 0.05, 0.5, 5.0, 50.0 |
| 5-Fluorouracil TM | Smith and Nephew | 0.1, 1.0, 10.0, 100.0 |
| Methotrexate TM | Quad Pharmaceuticals | 0.01, 0.1, 1.0, 10.0 |
| Mitomycin-C TM | Bristol-Myers | 0.01, 0.1, 1.0, 10.0 |
| Vinblastine TM | Quad Pharmaceuticals | 0.01, 0.1, 1.0, 10.0 |

6. Ficoll TM, 100 ml (LSM manufactured by Organon Teknika Corporation, Durham, N.C.)

Storage of Materials and Reagents 96-microwell extracellular matrix tissue culture plates, growth medium, and Percoll TM were stored at 2°-8° C. Drug strips were stored unopened at 2°-8° C. Ficoll TM and lysing buffer were stored at room temperature. Glutamine, pyruvate and asparagine were stored below −20° C. Reagents were brought to room temperature before use.

Specimen Collection and Transport

Surgical Specimens

Fluid Specimen Preparation

Ascites fluid was tapped into a vessel containing preservative-free sodium heparin (Invenex Laboratories Division of LyphoMed, Melrose Park, Ill. 60160) 10 units/ml ascites final volume. It should be noted that the presence of preservatives may inhibit the growth of tumor cells, and therefore should not be used to collect samples for use in this assay. Fluid specimens may remain unprocessed for 24–48 hours. For best results, however, begin the assay immediately.

Solid Specimen Preparation

Tumor tissue was handled aseptically at all times. For better results, the viable area of the tumor tissue should be isolated by trimming off fat and normal tissue, avoiding necrotic sections. 10 ml of transport medium (10% FBS in minimal essential medium (MEM) 500 ml) pipeted to a 50 ml conical tube was added to the trimmed tumor tissue. For better results, surgical specimens were minced to 1 mm within 30 minutes of removal. The assay should be begun immediately. If necessary, minced specimens may be held up to 16 hours after surgery, but no longer than 24 hours.

Specimen Preparation and Processing

Solid Specimen Processing

All specimen preparation steps were conducted in a laminar flow hood using aseptic technique. The specimen was removed from the transport medium using sterile forceps and placed in a 100 mm petri dish containing 5 ml tissue culture medium; RPMI+10% FBS. The specimen was minced, using a sterile scalpel, into pieces less than 1 mm in size. The tissue pieces were rinsed with 10 ml tissue culture medium and the medium was transferred, avoiding the larger tissue pieces, to a polystyrene tube. The tissue was washed repeatedly with 1 ml fresh tissue culture medium and then the rinses were added to a polystyrene tube. The number of tumor cells were counted. If an adequate cell number is obtained (see "Plating Density" section below), further processing was not necessary. If not, the sample should be processed further using the following steps. Transfer the minced specimen to a Cellector TM tissue sieve and gently force the specimen through the sieve by pressing downward with a glass pestle. Combine the tissue rinse to the tissue and medium collected from the tissue sieve and wash twice with tissue culture medium. If the tissue is too fibrous or collagenous and the cells cannot be dispersed by mechanical means such as the Cellector TM tissue sieve, digestive enzymes should be used to free single cells. A typical enzyme digestion includes use of a medium containing 0.08% collagenase and 0.002% DNase, incubating for 1-18 hours at 37° C. with gentle shaking. Cell viability should be monitored at 30 minute intervals for the first 2 hours. Viability should increase as the outer dead cells and connective tissue are digested. Allow the large pieces of tissue to settle and transfer the medium with suspended cells to a polystyrene conical tube. Wash the cells twice with tissue culture medium to remove enzymes, resuspending the cells in growth medium.

Tumor cell viability was assessed using a method such as a differential count using trypan blue and a hemacytometer. The total viable tumor cell count in the present assay must be at least $1-5 \times 10^5$ cells to test one drug plus controls. More cells were necessary for each additional drug tested.

After mechanical and enzymatic cell dispersion, the specimen may still required treatment to separate the tumor cells from the normal available, such as magnetic beads, Ficoll TM and/or Percoll TM gradients. The Ficoll TM and Percoll TM gradient cell separation methods are described here. If the cell suspension does not require further treatment, prepare the cell suspension to contain $1-5 \times 10^5$ cells/ml in growth medium. Eleven milliliters of the cell suspension were required in the present assay for each 96-well plate inoculated.

Fluid Specimen Preparation

All specimen preparation was conducted in a laminar flow hood using aseptic technique. The ascites fluid was mixed to achieve an even cell suspension by swirling. Only the fluid was transferred to centrifuge tubes and centrifuged at 400×g for 7 minutes. The supernatant was removed.

The cell pellet was resuspended and washed in growth medium, and centrifuged at 400×g for 7 minutes. All pellets were combined and resuspended in growth medium, Cyto-Gro TM 289 supplement + 1% FBS + RPMI.

Tumor cell viability was assessed using a method such as a differential count using trypan blue and a hemacytometer. The total viable tumor cell count must be at least $3 \times 10^5$ cells, for the present assay, to test one drug plus controls. More cells were necessary for each additional drug tested. Using the results of the differential count, the cell suspension was prepared. Eleven milliliters of the cell suspension were required for each 96-well plate inoculated.

Tumor Cell Enrichment

Ficoll TM Cell Separation- Note that this step is necessary if specimen contains more than 20% red blood cells.

Ficoll TM specimen processing was conducted in a laminar flow hood using sterile technique. 4 ml aliquots of Ficoll TM solution was dispensed (specific gravity 1.077) into conical polystyrene tubes. The specimen was suspended in tissue culture medium containing 10% fetal bovine serum (FBS) to attain a viable tumor cell. 10 ml of the specimen suspension was layered over the 4 ml aloquot of Ficoll TM. Note that these two solutions should not be mixed. The suspension was centrifuged at 1000×g for 15 minutes. The cell layer at the interface of the two solutions was removed and transferred to a clean conical polystyrene tube. The cell layer was centrifuged at 400×g for 7 minutes. The supernatant was discarded and the cell pellets were resuspended, washing the cells these times with tissue culture medium. The cell pellet was resuspended in the tissue culture medium and the viable tumor cells were counted using a differential count method such as trypan blue and a hemacytometer. Using the results of the differential count, a cell suspension was prepared to contain $3 \times 10^5$ cells/ml in growth medium. Eleven milliliters of the cell suspension was needed for each 96-well plate inoculated.

Percoll TM Gradient Cell Separation:- This step necessary if the specimen has a high percentage lymphocytes ($\geq 30\%$) and/or a high amount of cellular debris.

Percoll TM separation was conducted in a laminar flow hood using sterile technique. The Percoll TM solution was diluted at 90% to 10% and 20% using tissue culture medium. 10% and 20% Percoll TM solutions were prepared just prior to use. The number of gradients required for the entire specimen was calculated as follows. Each gradient can accommodate 2-3 ml containing up to $2 \times 10^7$ total cells. Prepare a 10%-20% Percoll gradient by aliquoting 4 ml of 10% Percoll TM in a polystyrene conical centrifuge tube. 4 ml of the 20% Percoll TM was layered under the 10% Percoll TM, being careful not to disturb the upper Percoll TM layer. The cell suspension obtained from the Ficoll TM separation was layered onto the Percoll TM gradient. The cellular suspension was centrifuged at 50-60 xg for 10 minutes at room temperature.

The majority of the tumor cells were observed to be pelleted in the bottom of the centrifuge tube. The lowest interface in the tube, however, may contain some tumor cells, that can be collected and inspected if desired. The higher interface contained mainly normal cells, such as leukocytes and may be discarded. The selected cell fractions were washed three times and resuspended with tissue culture medium. The tumor cells were counted using a differential cell count method such as trypan blue and a hemacytometer. A minimum viable tumor cell count of $3 \times 10^5$ cells was required to test one drug. More cells were required for additional drug testing. Using the results of the differential count, the cell suspension was prepared to contain $3 \times 10^5$ cells/ml of growth medium. Eleven milliliters of cell suspension was found to be required for each 96-well plate inoculated.

Positive and Background Assay Control

For each specimen, two columns of 16 wells were set aside for background and positive controls. The first column of 8 wells (1) were background control wells which remained cell- and drug-free serving as a baseline radioactivity control. As a result, the background control wells indicated how well the wash step removes tridiated thymidine from an extracellular matrix well. The positive control wells were the second column of 8 wells (2) and were inoculated with tumor cells, but remained drug-free. The positive control wells provided tritiated thymidine uptake data from a tumor cell population not treated with cancer chemotherapeutics.

Plating Density

Plating density per well were $1-2\times 10^4$ viable tumor cells per well for large cells such as ovarian and mesothelioma tumor cells, and $3-5\times 10^4$ viable tumor cells per well for small tumor cells such as small cell lung. Intermediate size tumor cells such as colon, prostate, bladder, breast and lung should be plated between $2-3\times 10^4$ viable tumor cells per well.

Plating Density Example:

If 5 drugs are tested, the total tumor cells requirements are as follows:

Controls: 8 wells $\times 1-5\times 10^4$ cells/well/100 $\mu l = 0.8-4\times 10^5$ cells 5 drug strips: 80 wells $\times 1-5\times 10^4$ cells/well/100 $\mu l = 8-40\times 10^5$ cells Total cells required $= 8.8-44\times 10^5$ cells

Cell Inoculation

Figure 1:
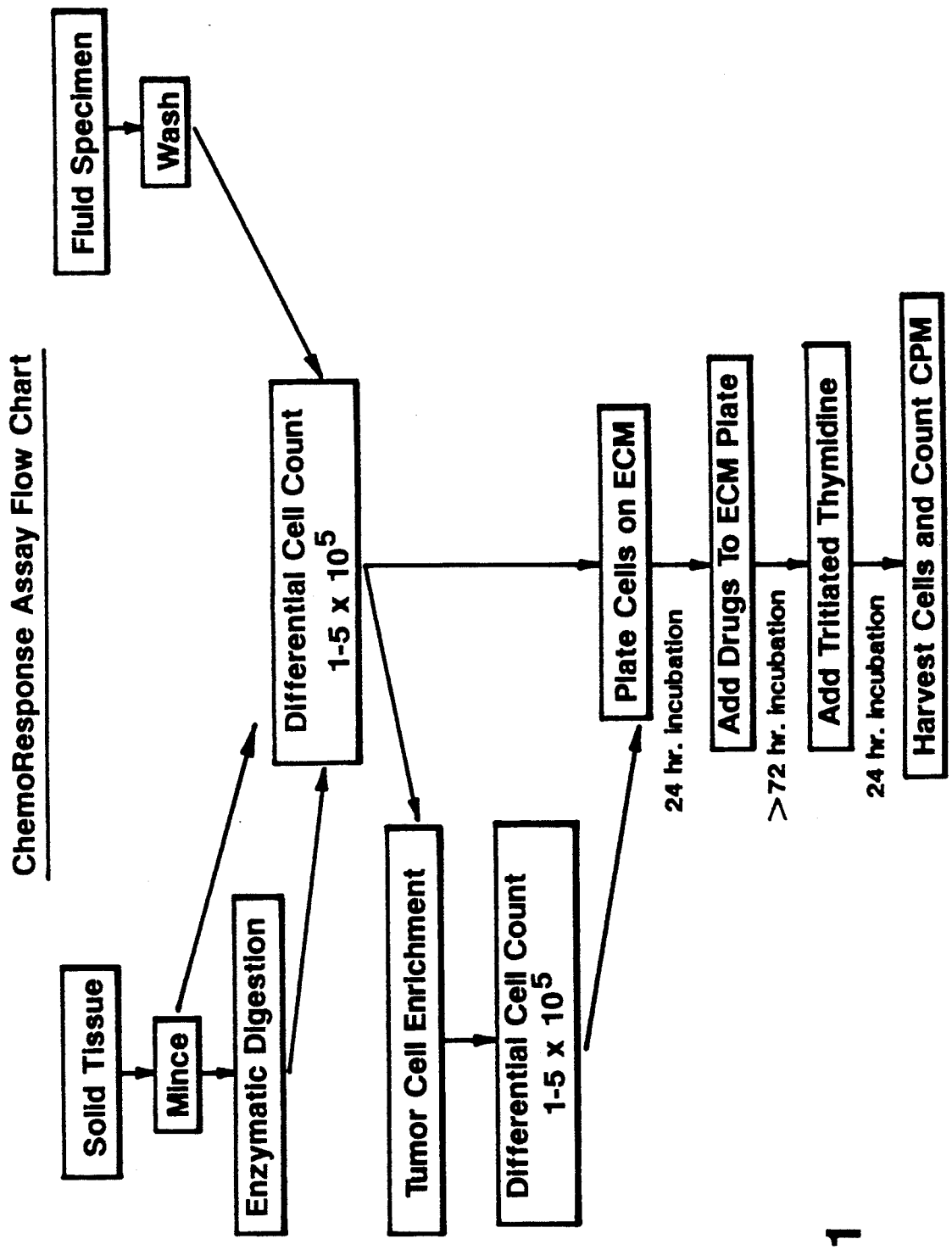
FIG. 1 shows the chemoresponse assay flow chart.

Cell inoculation was conducted in a laminar flow hood using sterile technique. The number of extracellular matrix microtiter plates required was calculated as follows. If one drug is tested, 24 wells must be inoculated, if two drugs are tested, 40 wells must be inoculated, etc. Positive and background control wells must be run with each specimen. Positive the background control wells in column 1, and the positive control wells in column 2 (FIG. 1).

The cells were evenly dispersed by inverting the tube with growth medium and cells 5-6 times. Inoculations were facilitated with the use of a multi-channel pipettor and V-shaped reservoir (Costar TM -Cambridge, Mass.). It is important that the dispensing procedure be completed in less than one minute to ensure an even distribution of cells. The positive control wells (column 2) were inoculated with cells. The background control wells were not inoculated with cells (column 1). 100 $\mu l$ of growth medium containing $1-5\times 10^5$ cells/ml of the tumor cell suspension was pipetted into the appropriate wells ($1-5\times 10^4$ cells per well total). The background control wells were not inoculated with cells. Note that pipet tips were changed for every cell transfer to decrease the risk of contamination. A multichannel pipettor facilitates ease of inoculation. Extracellular matrix plates were covered and incubated at 37° C. with 5% carbon dioxide for 24 hours in a humidified environment.

Drug Addition

The foil packaged drug strips were allowed to reach room temperature before opening. The package was opened in a laminar flow hood. The micro drug strips were removed from the foil pouch and placed in the plate frame with the labelled end at the bottom of the frame and snapped firmly into place. FIG. 3. The strip label was coded according to the particular drug. The control strip, labelled CS, was placed in columns 1 and 2 and the drug strips to be assayed in subsequent columns. Four concentrations of the drug are contained in each $2\times 8$ drug strip. The bottom 4 wells contained the lowest and the top 4 wells the highest drug concentration (see diagram below).

After placing all drug and control strips in the plate frame, (FIG. 3) 125 $\mu l$ of growth medium was added to each well. When reconstituting lyophilized drug, start with the lowest drug concentration wells and progress to the highest drug concentration. Pipet tips were changed before each medium addition. When assaying more than five drugs, a second plate frame is required. Additional control strips are not required for the second plate.

A homogeneous suspension was ensured by allowing the drugs to solubilize for five minutes and mixing by repeated aspirations. 100 $\mu l$ of the reconstituted drugs was pipetted to the appropriate wells containing cells. Note: do not inoculate control wells.

If testing more than one drug, pipet tips should be changed between drug strips. The vessels were covered, plated, incubated and humidified at 37° C., 5% carbon dioxide for three days, except when testing 5-Fluorouracil TM, a longer incubation time ($>96$ hours), and thus, a separate control must be used.

Tritiated Thymidine Assay

Prior to adding tritiated thymidine, the compartments of the vessel were observed for wells with consistent cell layer growth, microbial contamination and for wells which show toxic cells.

The amount of tritiated thymidine that was needed to run the assay was calculated: 25 $\mu l$ of tritiated thymidine was added to each well to achieve a final concentration per well of 1.0 microCurie. To achieve this, prepare a 1:25 dilution of stock tritiated thymidine (6.7 ci/mMol; 1.0 milliCurie/ml) in growth medium, resulting in a working strength concentration of 40 microCurie/ml. The addition of 25 $\mu l$ to a well will result in a concentration of 1microCurie/well. If an entire 96-well plate is assayed, $96\times 25$ $\mu l$ or at least 2.4 ml of the 1:25 dilution will be needed (i.e., 104 $\mu l$ stock tritiated thymidine + 2.5 ml growth media).

Preparation and addition of the tritiated thymidine: The appropriate amount of growth medium and tritiated thymidine was added to a tube. Pipet 25 $\mu l$ of the 40 microCurie/ml dilution was pipetted to each compartment, changing tips after each transfer. The plate was covered and incubated in a humidified environment at 37° C. 5% carbon dioxide for 10 to 16 hours.

Cell Harvesting

The harvester was prepared by washing the lines with approximately 40 ml 70% ethanol. The filter paper was placed in the harvester and the punch lowered. The filter paper was prewet by running approximately 25 ml water through the harvesting head. The plate to be harvested from the incubator was removed, and the harvesting head was placed into the first two rows, aspirating the contents of the wells. Water was dispensed through the harvesting head and washed until approximately four well volumes have passed (1 ml). 100 $\mu l$ of lysing buffer was added to these 24 wells, leaving the buffer on for two minutes.

The wells were thoroughly washed with water through the harvesting head with 6 to 8 well volumes (1.25 to 2 ml).

The harvesting head lines were cleaned with approximately 40 ml 70% ethanol. The harvester vacuum was switched to reverse and the filter striphead opened.

The 24 individual filters were placed into scintillation vials.

Steps 1 through 9 were repeated until all wells were harvested.

Approximately 2 ml scintillation fluid was added to the vials, capped and read in the scintillation counter.

Definition of evaluable samples

As assay is considered evaluable only if the following criteria are satisfied: the average CPM of the untreated control is ×1000 CPM; the average CPM is four times above the background CPM; the background CPM is <200 CPM; the coefficient of variation for the 8 control wells ((control standard deviation/control average)×100%) is <50%.

Data Interpretation

The background control value was the mean of the radioactivity counts from the 8 background control wells containing medium but no cells. This value served as a baseline radioactivity control to ensure that adequate harvester washes were achieved.

The positive control value was the mean of the radioactivity counts from the 8 positive control wells. Cells were added to the wells, but not chemotherapeutics and therefore the tritiated thymidine uptake by these cells represent maximum incorporation. The counts per minute (CPM) from the positive controls were considered 100%.

Test results were represented here as % control, calculated by dividing the CPM from drug treated wells with CPM from control wells, as below:

$$\frac{\text{Test Wells } CPM - \text{mean background } CPM}{\text{Positive Control wells } CPM - \text{mean background } CPM} \times 100\% = \% \text{ control}$$

A range of plasma and 1/10 plasma achievable drug concentrations are presented, represented by the hatched portion of the graph. SEE FIG. 4-8. For data interpretation, the % control value corresponding to the mean value of 1/10 plasma achievable drug concentration is used. Drugs which resulted in less than or equal to 20% of control growth, when used at 1/10 plasma achievable concentration, is considered sensitive. Drugs which inhibited less than 20% growth, having a CPM above 20% of the control value are considered resistant.

Figure 7:
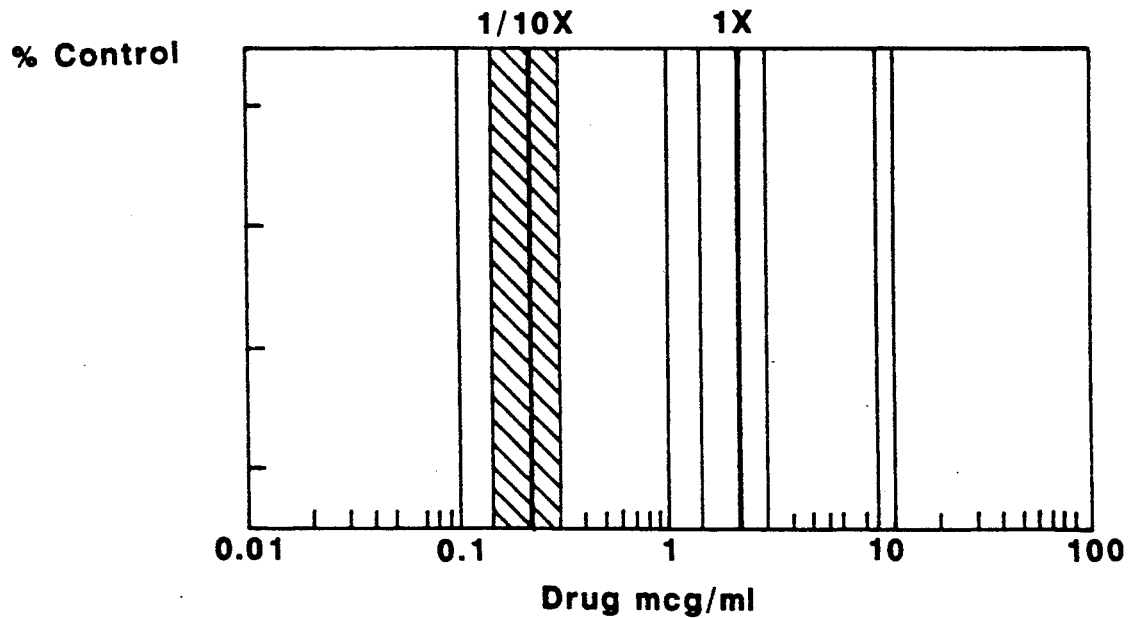
FIG. 7 shows assay results for sensitivity to Cispatinol TM.
Figure 8:
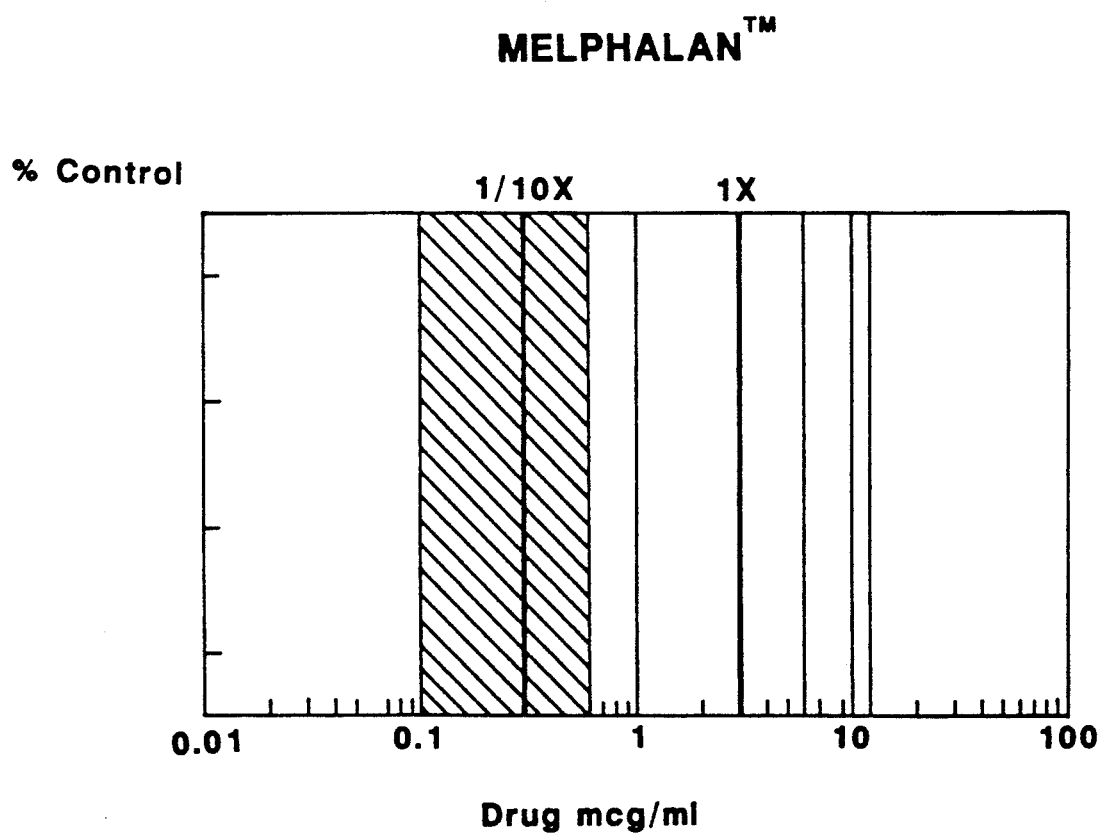
FIG. 8 shows assay results for sensitivity to Melphalan TM.

20% control (80% inhibition) is used as the positive/negative cut off value as it has been found to more closely correlate with clinical responses in similar in vitro drug response assay. David H. Kern, et al., *Development of a Miniaturized, Improved Nucleic Acid Procedure Incorporating Assay for Chemosensitivity Testing of Human Solid Tumor*, 45 Can. Res., 5436 (1985), Tanigawa, Nobuhiko, David H. Kern, Yorinori Hikase, and Donald L. Morton, *Rapid Assay for Evaluating the Chemosensitivity of Human Tumors in Soft Agar Culture*, Cancer Research, 42:2159-2164, 1982. ChemoResponse Assay results obtained from a surgical breast specimen have been plotted in FIGS. 4-8. The results indicate that the specimen is sensitive to Adriamycin, Bleomycin and 5-Fluorouracil (FIGS. 4-6) and resistant to Cisplatinol and Melphalan (FIGS. 7 and 8).

Although the invention has been shown in connection with certain specific embodiments, it will be readily apparent to those skilled in the art that various changes in form and arrangement of steps can be made to suit requirements without departing from the spirit and scope of the invention.

I claim:

1. A method for assaying the sensitivity of biopsied tumor cells to chemotherapeutic agents, the method comprising:
   a) incubating tumor cells with a sufficient amount of growth medium to form a cellular suspension and a predetermined amount of chemotherapeutic agents in a multi-compartment vessel, wherein the growth medium is formulated with calcium supplemented with growth factors, hormones and about 1% serum to selectively enhance the growth and proliferation of said tumor cells;
   b) adding an indicator of tumor cell growth or viability to certain compartments;
   c) measuring the amount of said indicator; and
   d) comparing the amount of said indicator in said compartment to which said chemotherapeutic agent was added with the compartment that did not receive said chemotherapeutic agent, to determine the sensitivity of said tumor cells for said chemotherapeutic agent.

2. The method of claim 1 wherein the calcium content is less than about 1 mM.

3. The method of claim 1 wherein said multi compartment vessel is selected from the group consisting of a microwell plate and a macrowell plate.

4. The method of claim 1 wherein said vessel is coated with a growth matrix.

5. The method of claim 4 wherein said matrix is derived from bovine cornea endothelium cells.

6. The method of claim 1 wherein said indicator is selected from the group consisting of a radioactive, enzymatic, chromogenic, phosphorescent, chemiluminescent and fluorescent indicator.

7. The method of claim 6 wherein said indicator is tritiated thymidine.

8. The method of claim 1 wherein a cell harvester is utilized to facilitate the measurement of the indicator.

9. A method for assaying the sensitivity of biopsied tumor cells to chemotherapeutic agents, comprising:
   a) incubating said tumor cells with a sufficient amount of growth medium to form a cellular suspension, wherein the growth medium is formulated with calcium supplemented with growth factors, hormones and about 1% serum to selectively enhance the growth and proliferation of said tumor cells;
   b) adding said cellular suspension to a first multi-compartment vessel;
   c) adding a predetermined amount of at least one chemotherapeutic agent in the dry form to a second multi-compartment vessel;
   d) adding a sufficient amount of said growth medium to reconstitute said dry chemotherapeutic agent to within physiologically reachable dosage ranges;
   e) adding said reconstituted chemotherapeutic agent to certain compartments of said first vessel containing tumor cells;
   f) incubating said chemotherapeutic agents in said first vessel for a sufficient period of time for said chemotherapeutic agents to affect said tumor cells;
   g) adding an indicator of tumor cell growth or viability to said first multi-compartment vessel;
   h) measuring the amount of said indicator; and
   i) comparing the amount of said indicator in said compartment to which said chemotherapeutic agent was added with the amount of said indicator in compartment that did receive said chemotherapeutic agent, to determine the sensitivity of said tumor cells for said chemotherapeutic agent.

10. The method of claim 9 wherein the calcium content is less than about 1 mM.

11. The method of claim 9 wherein said first multicompartment vessel is selected from the group consisting of a microwell plate and macrowell plate.

12. The method of claim 9 wherein predetermined amounts of said chemotherapeutic agent are added to said second vessel as a drug strip.

13. The method of claim 9 wherein said first vessel is coated with a growth matrix.

14. The method of claim 13 wherein said matrix is derived from bovine cornea endothelium cells.

15. The method of claim 9 wherein said indicator is selected from the group consisting of radioactive, enzymatic, chromogenic, phosphorescent, chemiluminescent and fluorescent indicator.

16. The method of claim 15 wherein said indicator is tritiated thymidine.

17. The method of claim 9 wherein a cell harvester is utilized to facilitate the measurement of the indicator.

* * * * *